US00PP21466P2

(12) United States Plant Patent
Delabroye

(10) Patent No.: US PP21,466 P2
(45) Date of Patent: Nov. 9, 2010

(54) ***HEUCHERA* PLANT NAMED 'KASSANDRA'**

(50) Latin Name: *Heuchera×villosa*
Varietal Denomination: Kassandra

(76) Inventor: Sandrine Delabroye, Rue Roger Salengro 40, Hantay (FR) F-59496

( * ) Notice: Subject to any disclaimer, the term of this patent is extended or adjusted under 35 U.S.C. 154(b) by 0 days.

(21) Appl. No.: 12/586,715

(22) Filed: Sep. 25, 2009

(51) Int. Cl.
*A01H 5/00* (2006.01)

(52) U.S. Cl. ..... Plt./440

(58) Field of Classification Search ..... Plt./263, Plt./440
See application file for complete search history.

*Primary Examiner*—Susan B McCormick Ewoldt
(74) *Attorney, Agent, or Firm*—Penny J Aguirre

(57) ABSTRACT

A new cultivar of *Heuchera×villosa*, 'Kassandra', characterized by its foliage that emerges coppery brown in color and changes to yellow-green and finally to a more golden color as it matures with distinct green veining, its large orbicular-shaped leaves on rosy red petioles, its compact and mounded plant habit, its tolerance to heat, humidity, and exposure to sunlight, and its hardiness in U.S.D.A Zones 4 to 9.

2 Drawing Sheets

Botanical classification: *Heuchera×villosa.*
Cultivar designation: 'Kassandra'.

BACKGROUND OF THE INVENTION

The present invention relates to a new and distinct cultivar of *Heuchera×villosa*, and is hereinafter referred to by the cultivar name 'Kassandra'.

The new cultivar was derived from a controlled breeding program by the Inventor in Hantay, France. The inventor made a cross in summer of 2006 between *Heuchera×villosa* 'Caramel' (U.S. Plant Pat. No. 16,560) as the female parent and *Heuchera×villosa* 'Mocha' (U.S. Plant Pat. No. 18,386) as the male parent. The Inventor selected 'Kassandra' in spring of 2007 as a single unique plant amongst the seedlings that resulted from the above cross.

Asexual reproduction of the new cultivar was first accomplished under direction of the inventor by in vitro propagation in Rijswijk, The Netherlands in May of 2009. Asexual reproduction of the new cultivar by division and tissue culture has shown that the unique features are stable and reproduced true to type in successive generations.

SUMMARY OF THE INVENTION

The following traits have been repeatedly observed and represent the characteristics of the new cultivar. These attributes in combination distinguish 'Kassandra' as a new and unique cultivar of *Heuchera.*

1. 'Kassandra' has foliage that is unique in color. The foliage emerges coppery brown in color and changes to yellow-green and finally to a more golden color as it matures with distinct green veining.
2. The leaves of 'Kassandra' are orbicular in shape and large in size and borne on petioles rosy red in color.
3. 'Kassandra' is tolerant to heat, humidity, and exposure to sunlight.
4. The plant habit of 'Kassandra' is mounded and compact.
5. 'Kassandra' is hardy in U.S.D.A. Zones 4 to 9.

'Kassandra' can be most closely compared to its parent plants. 'Caramel' is similar to 'Kassandra' in foliage color, however, 'Caramel' differs from 'Kassandra' in having smaller leaves and foliage that is more brown (caramel) when emerging and matures to a darker more olive green color, whereas the foliage of 'Kassandra' becomes more yellow-green in color before becoming golden in color as it matures. 'Mocha' is similar to 'Kassandra' in having large leaves however 'Mocha' differs from 'Kassandra' in producing an abundance of blooms and in having dark brown foliage, flowering for 'Kassandra' is sparse and not a distinguishing characteristic. 'Kassandra' can also be compared to the cultivar 'Marmalade' (U.S. Plant Pat. No. 15,945) for its similarity in foliage coloration in emerging a coppery brown color. 'Marmalade' differs from 'Kassandra' however in having foliage that becomes more orange red and less green as it matures, in having more undulating and ruffled foliage, and in producing an abundance of blooms.

BRIEF DESCRIPTION OF THE DRAWING

The accompanying colored photographs illustrate the overall appearance and distinct characteristics of the new *Heuchera.* The photographs were taken in The Netherlands of a two year-old plant as grown outdoors in a 20-liter container.

The photograph on FIG. 1 provides a view of the habit and foliage coloration of 'Kassandra' and the photograph in FIG. 2 provides a close-up view of a leaf of 'Kassandra'.

Figure 1:
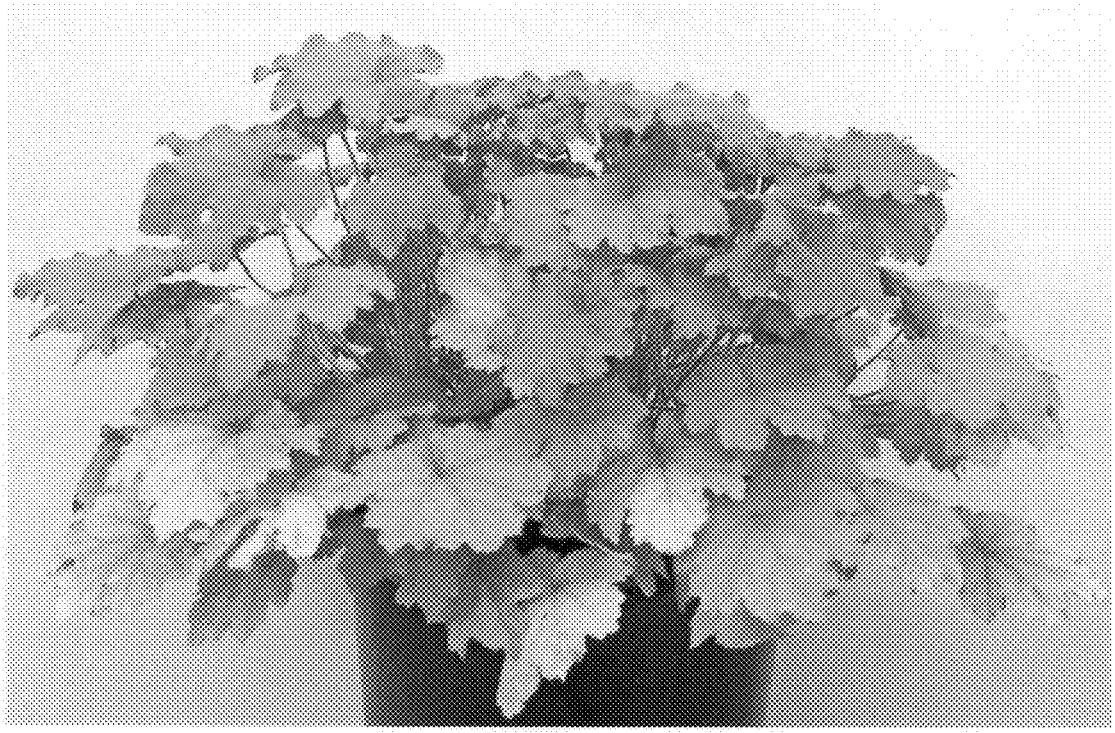
Figure 2:
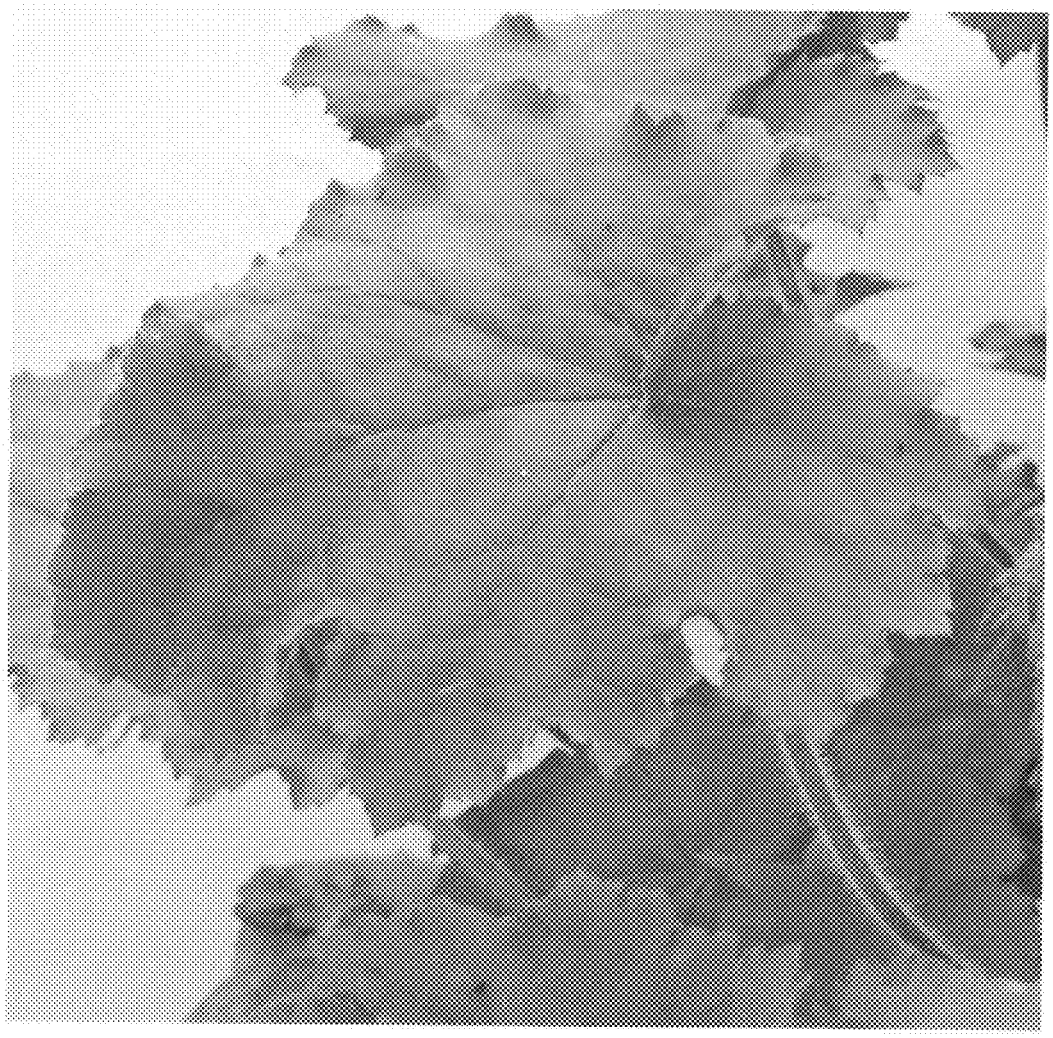

The colors in the photographs are as close as possible with the photographic and printing technology utilized. The colors in the photograph may differ slightly from the color values cited in the detailed botanical description, which accurately describe the colors of the new *Heuchera.*

DETAILED BOTANICAL DESCRIPTION OF THE PLANT

The following is a detailed description of a two year-old plant of the new cultivar as grown outdoors in a 20-liter container in The Netherlands. The phenotype of the new cultivar may vary with variations in environmental, climatic, and cultural conditions, as it has not been tested under all possible environmental conditions. The color determination is in accordance with the 2007 R.H.S. Colour Chart of The Royal Horticultural Society, London, England, except where general color terms of ordinary dictionary significance are used.

General description:

*Botanical classification.*—'Kassandra' is a cultivar of *Heuchera×villosa*.

*Plant habit.*—Compact, clump-forming herbaceous perennial, mounded foliage.

*Height and spread.*—Reaches about a height of about 40 cm in height and about 82 cm in width.

*Hardiness.*—U.S.D.A. Zone 4 to 9.

*Diseases and pests.*—Disease free in the conditions tested, no susceptibility or resistance to pests has been observed.

*Root description.*—Fibrous roots on woody rootstalks.

*Branching habit.*—Basal rosettes of leaves on petioles.

*Propagation.*—In vitro propagation is the preferred method, division are also possible.

*Growth rate.*—Moderate to vigorous.

Foliage description:

*Leaf shape.*—Orbicular.

*Leaf division.*—Simple.

*Leaf base.*—Strongly cordate (leaves at base overlap).

*Leaf apex.*—Acute.

*Leaf venation.*—Primary palmate, secondary net-veined, color on upper surface 146B and 146D, color on lower surface of mature leaves is N160D becoming conspicuous on upper surface as the leave matures.

*Leaf margins.*—Lobed with 5 to 7 lobes with lobes crenate.

*Leaf attachment.*—Petiolate.

*Leaf arrangement.*—Basal rosettes.

*Leaf orientation.*—Held horizontal to petiole, slightly undulating.

*Leaf surface.*—Dull and pubescent with 1 mm stiff white hairs on margins, upper surface, and on veins of lower surface.

*Leaf color.*—Upper surface emerging; 174A, upper surface mature; 152A and 152B becoming 153A, upper surface mature; 162A and 162B, lower surface emerging; 184C, lower surface maturing and mature 181C.

*Leaf size.*—An average of 15 cm in length and 13.9 cm in width.

*Leaf quantity.*—About 300 per plant two years in age.

*Petioles.*—Round in shape, an average of 25.8 cm in length and 3 mm in width, 182A in color, pubescent surface.

*Stipules.*—None observed.

Flower and seed description: Flowering was been observed under the conditions grown for data collection, flowering has been sparse, insignificant, and not a distinguishing characteristic of 'Kassandra'.

It is claimed:

1. A new and distinct cultivar of *Heuchera* plant named 'Kassandra' as herein illustrated and described.

* * * * *